United States Patent
Suwito et al.

(10) Patent No.: US 11,191,889 B2
(45) Date of Patent: Dec. 7, 2021

(54) ANTI-SNAGGING INFUSION SETS

(71) Applicant: CareFusion 303, Inc., San Diego, CA (US)

(72) Inventors: Wantjinarjo Suwito, Irvine, CA (US); Corey Mark Christensen, Anaheim, CA (US); Christopher Jesse Zollinger, Chino Hills, CA (US)

(73) Assignee: CAREFUSION 303, INC., San Diego, CA (US)

( * ) Notice: Subject to any disclaimer, the term of this patent is extended or adjusted under 35 U.S.C. 154(b) by 94 days.

(21) Appl. No.: 16/224,577

(22) Filed: Dec. 18, 2018

(65) Prior Publication Data

US 2020/0188576 A1 Jun. 18, 2020

(51) Int. Cl.
*A61M 5/14* (2006.01)

(52) U.S. Cl.
CPC ........ *A61M 5/1413* (2013.01); *A61M 5/1415* (2013.01); *A61M 5/1418* (2013.01)

(58) Field of Classification Search
CPC .............. A61M 5/1413; A61M 5/1415; A61M 5/1418; A61M 5/1411; A61M 5/1689; A61M 5/14; A61M 5/162; A61M 1/3627; A61M 39/10; A61M 39/26; A61M 39/06; A61M 39/14; A61J 1/00; A61J 1/05; A61J 1/201; A61J 1/2096; A61J 1/20
See application file for complete search history.

(56) References Cited

U.S. PATENT DOCUMENTS

| | | | | |
|---|---|---|---|---|
| 4,056,333 | A | * | 11/1977 | Lundquist ......... A61M 5/16854 417/44.2 |
| 4,685,912 | A | * | 8/1987 | Jones ................... A61M 5/1411 128/DIG. 12 |
| 5,126,054 | A | | 6/1992 | Matkovich |
| 5,356,396 | A | * | 10/1994 | Wyatt .................... A61M 39/04 604/539 |
| 5,573,280 | A | | 11/1996 | Salter et al. |
| 6,485,483 | B1 | | 11/2002 | Fuji |
| 7,585,288 | B2 | | 9/2009 | Haberland et al. |

(Continued)

FOREIGN PATENT DOCUMENTS

| CA | 2193702 A1 | 1/1996 |
|---|---|---|
| WO | WO-2018181270 | 10/2018 |

OTHER PUBLICATIONS

International Search Report and Written Opinion for Application No. PCT/US2019/065894, dated Apr. 29, 2020, 19 pages.

*Primary Examiner* — Amber R Stiles
*Assistant Examiner* — Alexandra Lalonde
(74) *Attorney, Agent, or Firm* — Morgan, Lewis & Bockius LLP (57) ABSTRACT

Anti-snagging components for use in infusion sets are provided. The anti-snagging component includes a sliding surface that guides an infusion set component past an obstruction when the infusion set is moved during manufacture or use. An anti-snagging structure may be integrally formed as a portion of an infusion set component or the anti-snagging structure may be a separate component that connects or attaches to an infusion set component. Some anti-snagging structures include a covering portion to cover a needleless connector and a tail portion to connect to a length of tubing. The covering portion may include an anti-microbial coating.

6 Claims, 8 Drawing Sheets

(56) References Cited

U.S. PATENT DOCUMENTS

2004/0002684 A1* 1/2004 Lopez .................. A61J 1/2096
604/240
2006/0217671 A1 9/2006 Peppel
2016/0354594 A1* 12/2016 Uehara ................ A61M 39/10

* cited by examiner

ANTI-SNAGGING INFUSION SETS

CROSS-REFERENCES TO RELATED APPLICATIONS

N/A

BACKGROUND

Infusion sets are used in the medical field for inserting liquid substances into a patient. Infusion sets are typically constructed by joining multiple translucent polymeric tubing segments to multiple polymeric components. The joints are formed by applying a thin layer of solvent or adhesive on one or both of contacting surfaces and the two surfaces are brought together. Generally, the external shapes of infusion sets have many steps or transition points without smooth transitions. In some cases, the joints/components form acute angles that are prone to get caught on stationary edges or objects.

Infusion sets are moved from one station to another during manufacturing, potentially, with components dangling down. Thus, the infusion sets can get caught on bench top edges or manufacturing equipment. In use, infusion sets can also be moved about extensively, such as when patients are hooked up with an infusion set and a mobile apparatus so that the patients can walk around. Either in manufacturing or in use, if one of the infusion set components is caught on a stationary object, then it results in tugging the line. If there is a weak joint, or still curing joints, then a leak or separation in the infusion set occurs. This can lead to a mere inconvenience to something more serious. It is desirable to provide infusion sets with reduced or eliminated snagging points.

SUMMARY

The present disclosure provides infusion sets having with anti-snagging structures to reduce or eliminate snagging of the infusion set during manufacture, storage or use. Components of the infusion may have integral anti-snagging structures and/or anti-snagging components added-on to standard infusion sets or infusion set components.

In one or more embodiments, an anti-snagging component for use in an infusion set is provided. The anti-snagging component includes a housing having a fluid input end and a fluid output end and an anti-snagging structure disposed at one of the fluid input end and the fluid output end. The anti-snagging structure includes a tube port extending from an end surface of the housing, the tube port configured to receive an end portion of a length of tubing. The anti-snagging structure also includes at least one sliding structure disposed on the end surface of the housing, the at least one sliding structure extending from the end surface of the housing to an end portion of the tube port, wherein a sliding surface of the sliding structure is configured to slidingly guide the housing past an obstruction without snagging when the infusion set is moved.

In one or more aspects, the anti-snagging component is a drip chamber with the anti-snagging structure disposed at the fluid output end. In one or more aspects, the anti-snagging component is a check valve with a first anti-snagging structure disposed at the fluid output end and a second anti-snagging structure disposed at the fluid input end. In one or more aspects, the sliding structure is a gusset having a curvilinear triangular shape with a first side disposed on the tube port, a second side disposed on the end surface of the housing and a hypotenuse having a curvilinear sliding surface. In one or more aspects, the sliding structure is four gussets equally spaced apart about the end surface of the housing. In one or more aspects, the curvilinear sliding surface is concave or convex. In one or more aspects, the sliding structure is a three-dimensional conical shape having a curvilinear sliding surface In one or more embodiments, an anti-snagging component for use in an infusion set is provided. The anti-snagging component includes a housing having first and second fluid input ends and a fluid output end, each configured to receive an end portion of a length of tubing. The anti-snagging component includes an anti-snagging structure disposed at the first fluid input end. The anti-snagging structure includes a first structure end connected to the first fluid input end, wherein the first input end is configured to receive an input tube, a second structure end extending away from the first structure end, the second structure end configured to connect to the input tube, and a sliding surface disposed between the first and second structure ends, the sliding surface configured to slidingly guide the housing past an obstruction without snagging when the infusion set is moved.

In one or more aspects, the anti-snagging component is a Y-junction and the sliding surface is a convex curvilinear shape. In one or more aspects, the anti-snagging component is a Y-site having a needleless connector disposed at the second fluid input end and the sliding surface is a convex curvilinear shape.

In one or more embodiments, an anti-snagging component for use in an infusion set is provided. The anti-snagging component includes a covering portion configured to be received by a needless connector on a first input end of a Y-site infusion set component, a tail portion configured to be slidingly connected to an input tube received by a second input end of the Y-site infusion set component, and a sliding surface configured to slidingly guide the Y-site infusion set component past an obstruction without snagging when the infusion set is moved. The covering portion is configured to cover an access point of the needleless connector when the anti-snagging component is engaged with the Y-site infusion set component and the covering portion is removed from the access point of the needleless connector when the anti-snagging component is disengaged from the Y-site infusion set component.

In one or more aspects, the tail portion is comprised of a flexible material. In one or more aspects, the covering portion is a slip-on cap configured to slip over at least the top portion of the needleless connector. In one or more aspects, the slip-on cap has one or more slits to open up the slip-on cap when it is fit over the top portion of the needleless connector. In one or more aspects, the slip-on cap is comprised of a flexible material that stretches when it is fit over the top portion of the needleless connector. In one or more aspects, the slip-on cap includes a top surface configured to cover the top surface of the needleless connector and a partial side wall configured to cover only a portion of a circumference of the needleless connector. In one or more aspects, the covering portion is a screw-on cap configured to screw onto threads of the needleless connector. In one or more aspects, the covering portion is a hood configured to slip over both the first and second input ends of the Y-site infusion set component. In one or more aspects, the covering portion comprises an anti-microbial coating disposed on an inner surface, the anti-microbial coating configured to contact the access point of the needleless connector when the anti-snagging component is engaged with the needleless connector.

Additional features and advantages of the disclosure will be set forth in the description below and, in part, will be apparent from the description or may be learned by practice of the disclosure. The objectives and other advantages of the disclosure will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
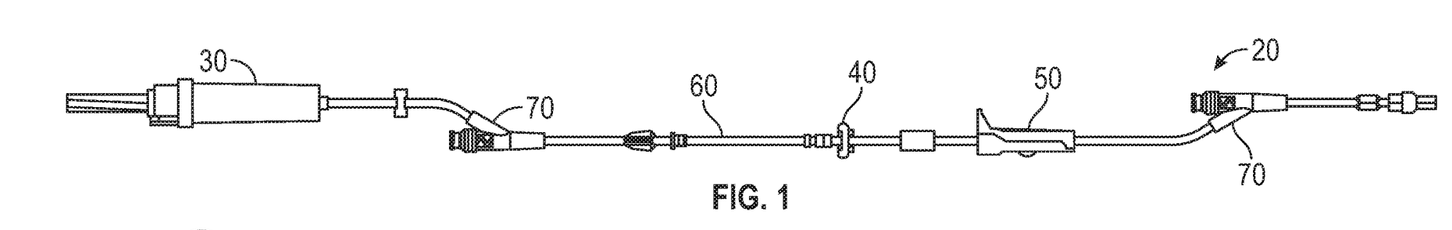
FIG. 1 depicts a schematic view of an example infusion set.

Infusion sets may be formed from any combination of infusion components and tubing. Typically, the infusion components and tubing are disposable products that are used once and then discarded. The infusion components and tubing may be formed from any suitable material (e.g., plastic, silicone, rubber). As shown in FIGS. 1-2D, an infusion set 20 may include a drip chamber 30, a check valve 40 and a roller clamp 50 connected together by tubing 60. Infusion set 20 may also include a Y-site 70 having a Y-shaped junction with an inlet port 72 connected to an inlet tube 62, a needleless connector 75 and an outlet port 74 connected to an outlet tube 64. The needleless connector 75 provides a port for the introduction of fluid into and/or removal of air bubbles from the infusion set 20. For example, a needleless syringe (not shown) may be connected to the needleless connector 75 in order to add medication to a saline fluid that is gravity fed from a saline bag (not shown) into the drip chamber 30. The infusion set 20 may include additional infusion components and may be formed of any combination of components and the tubing 60.

Figure 2A:
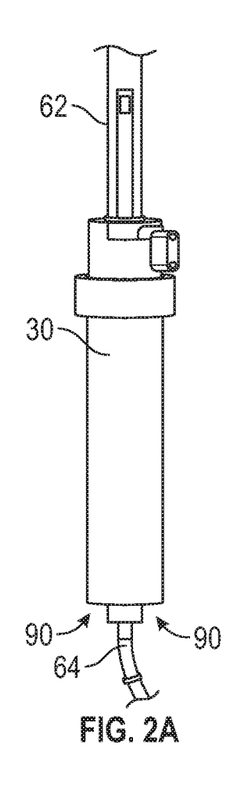
FIGS. 2A-2D depicts example infusion set components and joints with a potential for snagging.
Figure 2B:
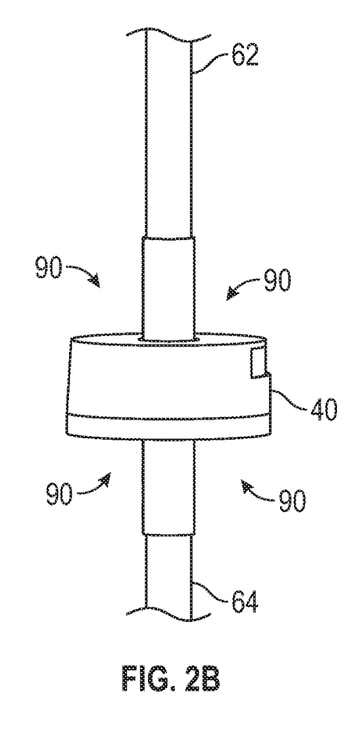
Figure 2C:
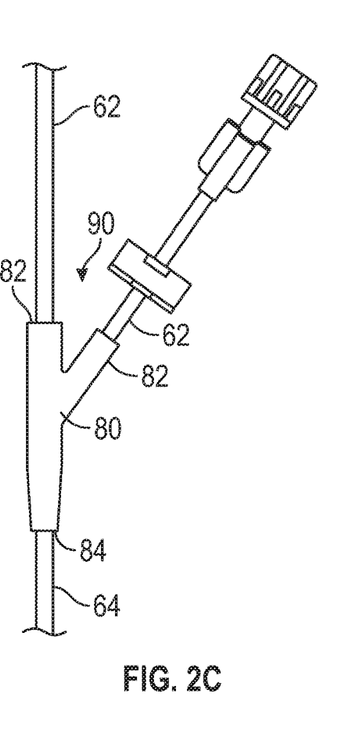
Figure 2D:
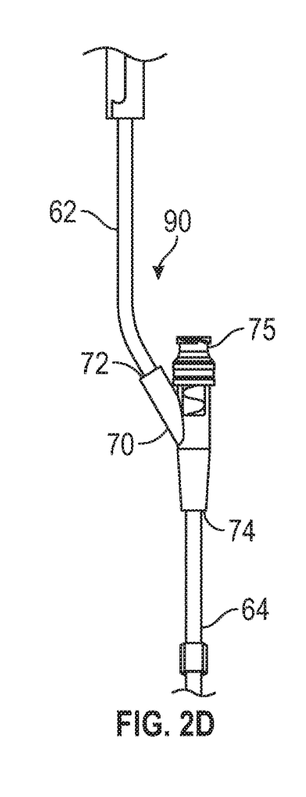

As shown in more detail in FIG. 2A, the drip chamber 30 is connected to an inlet tube 62 and an outlet tube 64. Similarly, in FIG. 2B the check valve 40 is connected to an inlet tube 62 and an outlet tube 64. FIG. 2C shows a Y-junction 80 having two inlet ports 82 and one outlet port 84, where each inlet port 82 is connected to an inlet tube 62 and the outlet port 84 is connected to an outlet tube 64. The Y-site 70 shown in FIG. 2D has an inlet port 72 connected to an inlet tube 62, an outlet port 74 connected to an outlet tube 64 and a needleless connector 75.

Each of the infusion components and junction points of the infusion set 20 provide angled surfaces that may be snagged or engaged by equipment and/or surfaces during manufacture of the infusion set. Similarly, the infusion components and junction points of the infusion set 20 may also be snagged by medical equipment and/or patients/caregivers during usage of the infusion set 20. For example, end surfaces of the drip chamber 30 and the check valve 40 are perpendicular to the tubing 60, providing snagging points 90 as shown in FIGS. 2A and 2B. Similarly, the Y-junction 80 and the Y-site 70 also have snagging points 90, as shown in FIGS. 2C and 2D.

Figures 3, 4A, 4B, 4C:
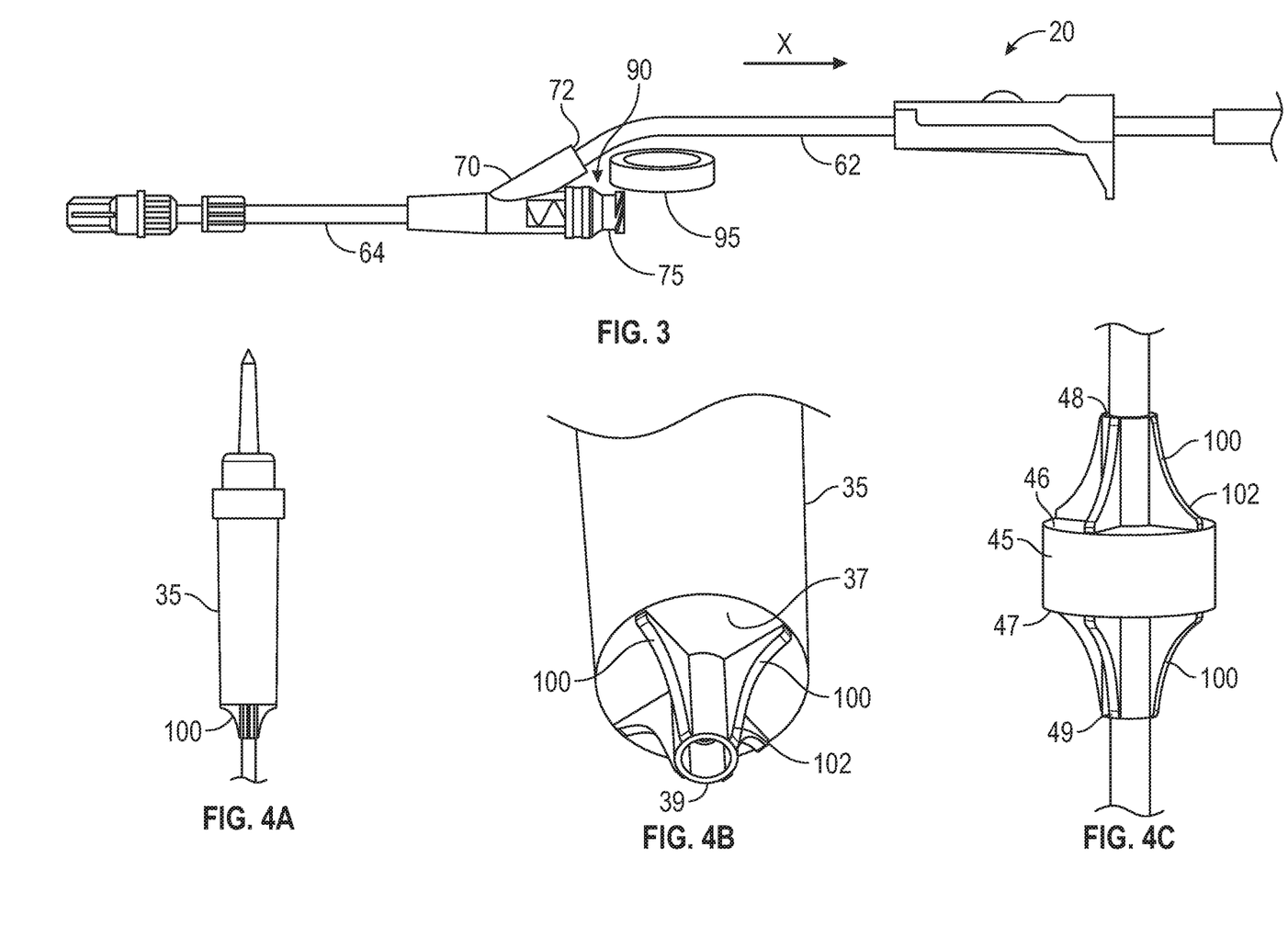
FIG. 3 depicts a schematic view of an example infusion set movement with a joint/component snagging on a stationary object.
FIGS. 4A-4C depict schematic views of one or more embodiments of anti-snagging infusion set components.

FIG. 3 shows an example of snagging of a Y-site 70 when the infusion set 20 is being moved in a direction X. Here, as the infusion set 20 is moved (e.g., pulled) in direction X, the snagging point 90 formed by the junction between the inlet port 72 and the needleless port 75 engages with (e.g., is snagged by) a physical object 95 (e.g., a table edge, a piece of medical equipment, a hospital bed frame). Depending on the pulling force in the direction X, the inlet tube 62 may pull free or loosen from the inlet port 72, thus leading to a defective infusion set 20 during manufacture or an infusion set 20 having a leak or failure during use.

As shown in FIGS. 4A-4C, infusion components may include an anti-snagging structure gusset 100. The gusset 100 may be integrally formed as part of an infusion component or the gusset 100 may be added to an existing infusion component. The gusset 100 may fill a portion or all of the space that defines the snagging point 90 described above. For example, FIGS. 4A and 4B show a drip chamber 35 with multiple gussets 100 formed on the bottom of the drip chamber 35. Each gusset 100 may have a curvilinear shape that provides an anti-snagging surface (e.g., sliding surface) 102 that slides along and over a physical object during movement of the infusion set 20. Similarly, a check valve 45 may have gussets 100 formed on both the top and bottom of the check valve 45 to prevent snagging of the check valve 45 by a physical object when moving in either direction.

The gusset 100 may be any shape (e.g., triangular, convex, concave) that provides the sliding surface 102 over which an object may slide without snagging. The sliding surface 102 may extend from across an area that would define a snagging point (e.g., snagging point 90) in the absence of the gusset 100. For example, the sliding surface 102 of the gussets 100 on the drip chamber 35 extend from a drip chamber end surface 37 to an outlet port end surface 39 as shown in FIG. 4B. Similarly, as shown in FIG. 4C, the sliding surface 102 of some of the gussets 100 on the check valve 45 extend from a check valve end surface 46 to an inlet port end surfaces 48, and other gussets 100 on the check valve 45 extend from a check valve end surface 47 to an outlet port end surface 49. As shown in FIGS. 4A-4C, each of the drip chamber 35 and the check valve 45 have four gussets 100 spaced apart at ninety degree angles, however, the disclosure is not limited as such. Accordingly, any number of gussets 100 may be used and the gussets 100 may be disposed in any desired positioning or spacing.

Figures 5A, 5B:
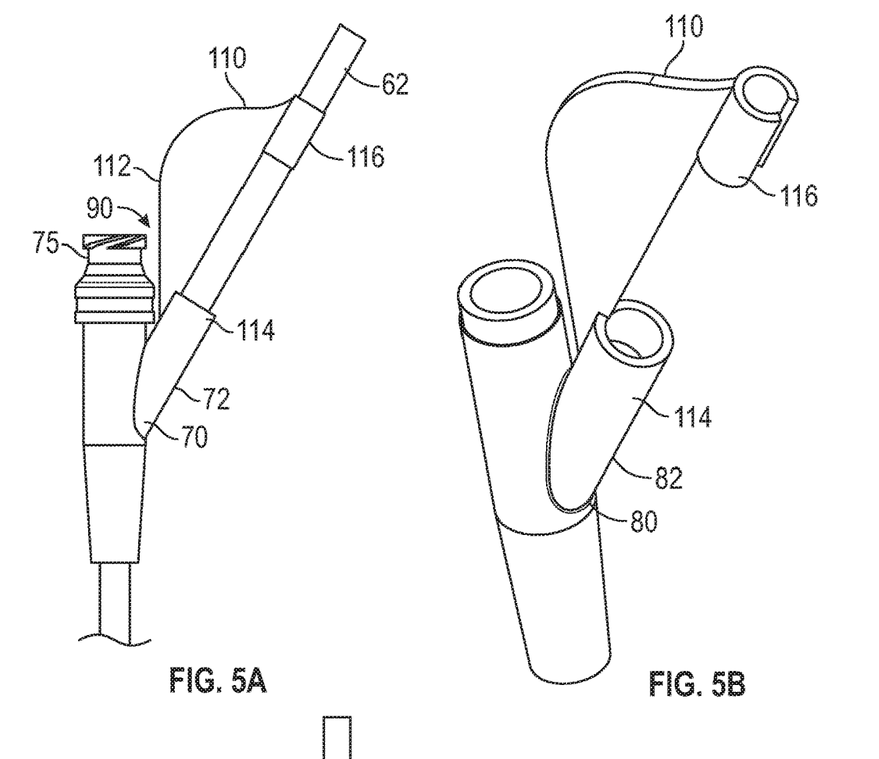
FIGS. 5A-5C depict schematic views of one or more embodiments of an anti-snagging infusion set joint components.
Figure 5C:
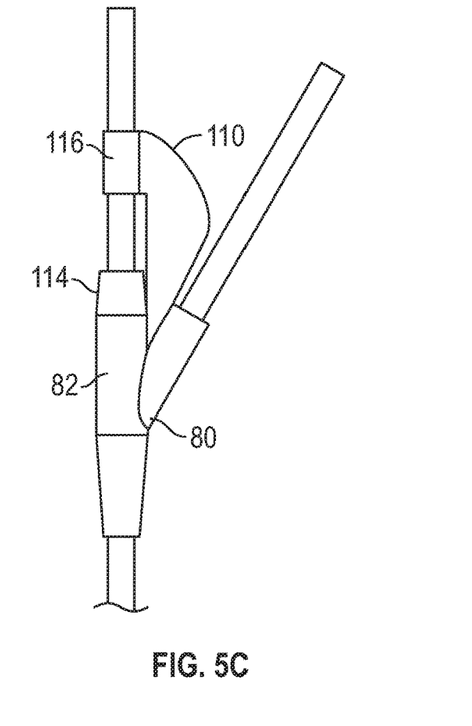

As shown in FIGS. 5A-5C, an anti-snagging structure webbing 110 is provided. The webbing 110 may be integrally formed as part of an infusion component, the webbing 110 may be added to an existing infusion component and/or the webbing 110 may be formed as a separate component to be added to the infusion set 20. The webbing 100 may be any desired shape and size. The webbing 100 may be configured to connect to the tubing 60 of the infusion set 20. For example, as shown in FIG. 5A, a Y-site 70 includes the webbing 110 having a bell-curve shape with one end 114 connected at the input port 72 and another end (e.g., connection point) 116 connected to the input tube 62. Here, the webbing 110 is positioned such that a sliding surface 112 causes a physical object to slide away from the Y-site 70 and avoid snagging on the snagging point 90 or the needleless connector 75. A similar webbing 110 is shown for a Y-junction 80 as shown in FIG. 5B. Here, the webbing 110 has a bell-curve shape with one end 114 connected at an input port 82 and another end 116 connected at the input tube 62. In yet another example, a Y-junction 80 may have a partially semicircular shaped webbing 110 connected to an input port 82.

The examples shown in FIGS. 5A-5C are not limiting. For example, the webbing 110 may have any shape and size with a sliding surface 112 that is configured to move the infusion component past a physical object without snagging. In addition, the webbing 110 may be a separately formed infusion set component where both ends of the webbing 110 connect to tubing 60 and the webbing 110 may slide along the tubing 60 until positioned next to a Y-site 70, a Y-junction 80 or any other infusion component.

Figure 6A:
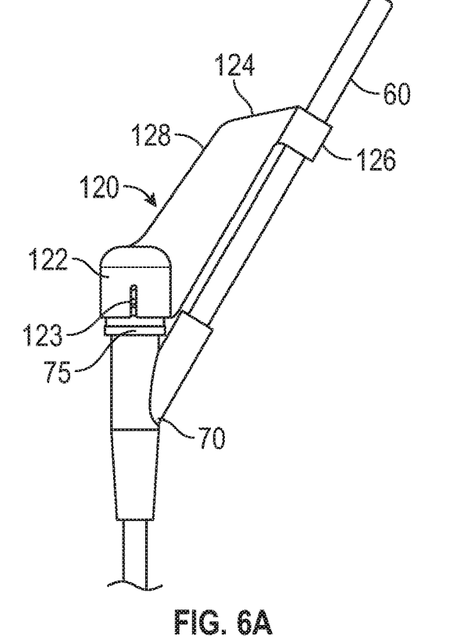
FIGS. 6A and 6B depict schematic views of one or more embodiments of an anti-snagging infusion set component in engaged and disengaged positions.
Figure 6B:
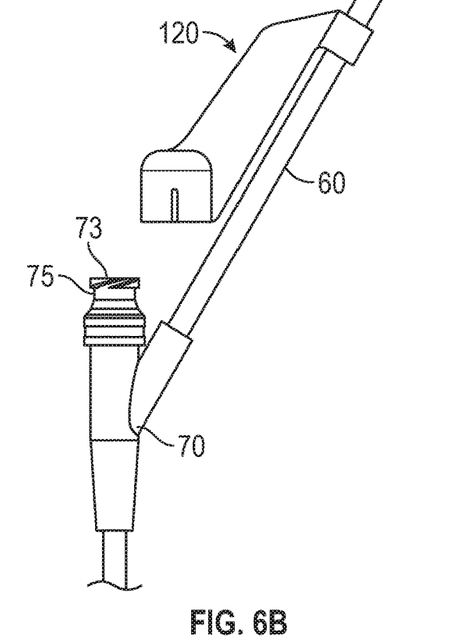

As shown in FIGS. 6A and 6B, an anti-snagging structure (e.g., cap) 120 is provided. The cap 120 may have a covering portion (e.g., cap portion) 122 and a tail portion 124. The cap portion 122 may be a slip-on cap that is configured to slip over a needleless connector 75 of a Y-site 70. The cap portion 122 may be a deformable or flexible (e.g., soft) material that stretches as it fits over the needleless connector 75. The cap portion 122 may have one or more slits 123 so that the cap portion 122 opens up to some degree (e.g., expands the circumference of the leading edge) as the cap portion 122 fits over the needleless connector 75. The tail portion 124 may be flexible and have a tube connection point 126 for tethering the tail portion 124 to a tube 60 (e.g., input tube 62). The tail portion 124 has a sliding surface 128 configured to move the Y-site 70 past a physical object without snagging. The cap 120 may slide onto the tube 60 and then slide towards the Y-site 70 until the cap portion 122 is snapped onto the needleless connector 75. In addition to preventing snagging of the Y-site 70 when the cap 120 is in position, the cap portion 122 has the additional benefit of covering the needleless connector 75, thus reducing or eliminating contact with contaminants. The cap portion 122 may include a coating (e.g., chlorohexidine) configured to act as an antimicrobial on an access point 73 of the needleless connector 75.

Figure 7A:
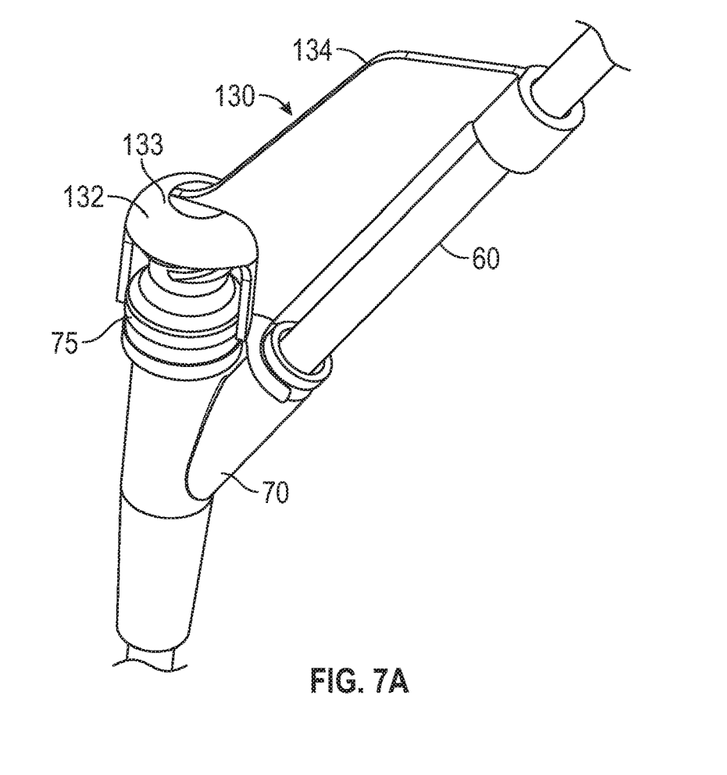
FIGS. 7A and 7B depict schematic views of one or more embodiments of an anti-snagging infusion set component in engaged and disengaged positions.
Figure 7B:
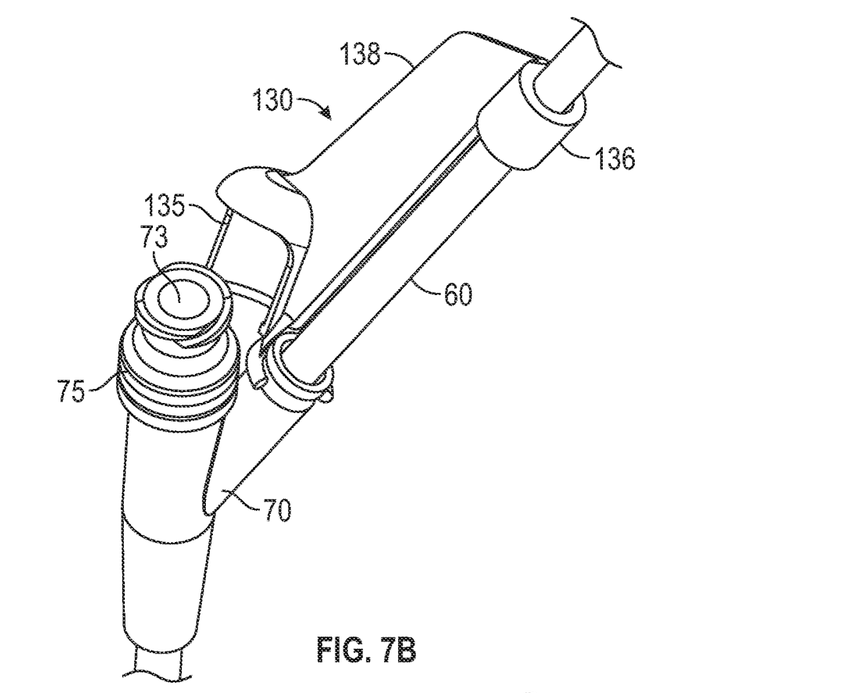

As shown in FIGS. 7A and 7B, an anti-snagging structure (e.g., cap) 130 is provided. The cap 130 may have a covering portion (e.g., cap portion) 132 and a tail portion 134. The cap portion 132 may be a slip-on cap that is configured to slip over a needleless connector 75 of a Y-site 70. The cap portion 132 may have a top surface 133 that fits over a top surface (e.g., the access point) of the needleless connector 75 and a side wall 135 that is partially open such that the side wall 135 does not encircle the entire perimeter of the needleless connector 75. The tail portion 134 may have a tube connection point 136 for tethering the tail portion 134 to a tube 60 (e.g., input tube 62). The tail portion 134 has a sliding surface 138 configured to move the Y-site 70 past a physical object without snagging. The cap 130 may slide onto the tube 60 and then rotate around the tube 60 until the cap portion 132 is snapped onto the needleless connector 75. In addition to preventing snagging of the Y-site 70 when the cap 130 is in position, the cap portion 132 has the additional benefit of covering the access point 73 of the needleless connector 75, thus reducing or eliminating contact with contaminants. The cap portion 132 may include a coating (e.g., chlorohexidine) configured to act as an antimicrobial on an access point 73 of the needleless connector 75.

Figure 8A:
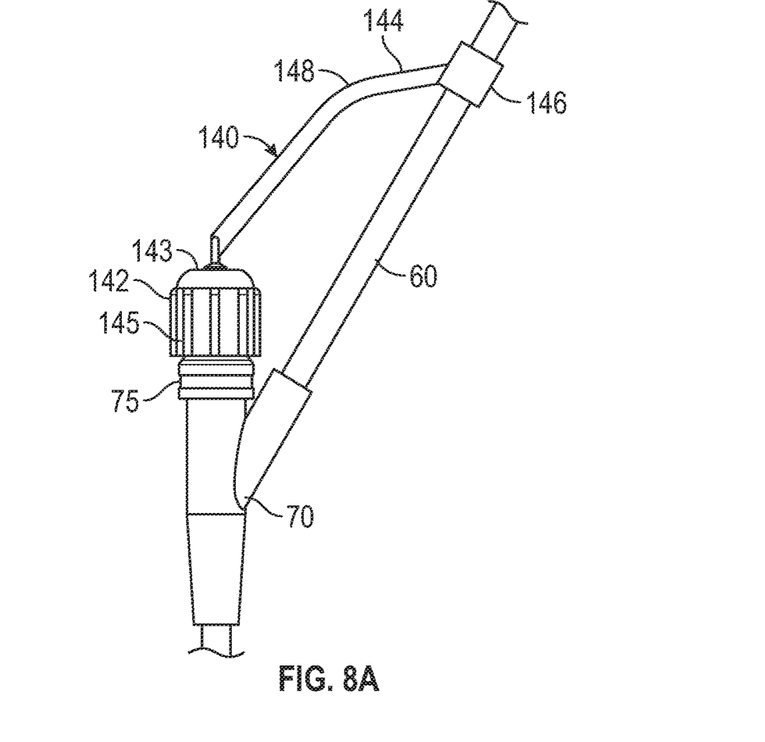
FIGS. 8A-8C depict schematic views of one or more embodiments of an anti-snagging infusion set component in engaged and disengaged positions.
Figure 8B:
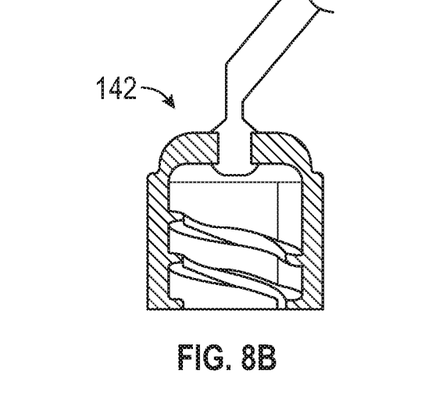
Figure 8C:
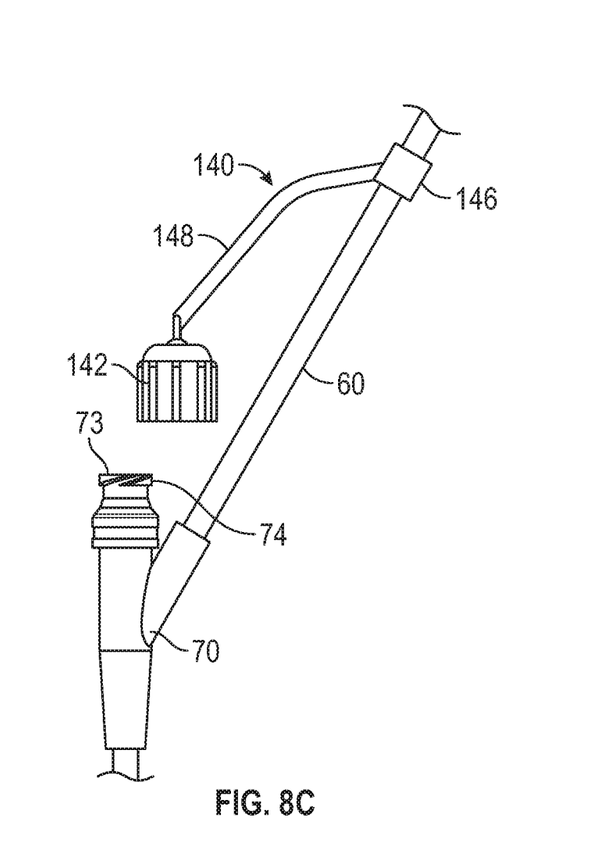

As shown in FIGS. 8A-8C, an anti-snagging structure (e.g., cap) 140 is provided. The cap 140 may have a covering portion (e.g., cap portion) 142 and a tail portion 144. The cap portion 142 may be a screw-on cap that is configured to screw onto threads 74 of a needleless connector 75 of a Y-site 70. The cap portion 142 may have a top surface 143 that fits over a top surface of the needleless connector 75 and a side wall 145 that fully encircles the perimeter of the needleless connector 75. The tail portion 144 may have a tube connection point 146 for tethering the tail portion 144 to a tube 60 (e.g., input tube 62). The tail portion 144 has a sliding surface 148 configured to move the Y-site 70 past a physical object without snagging. The tube connection point 146 of the cap 140 may slide onto the tube 60 and slide down the tube 60 to bring the cap portion 142 into position to be threaded onto the needleless connector 75. In addition to preventing snagging of the Y-site 70 when the cap 140 is in position, the cap portion 142 has the additional benefit of covering the access point 73 of the needleless connector 75, thus reducing or eliminating contact with contaminants. The cap portion 142 may include a coating (e.g., chlorohexidine) configured to act as an antimicrobial on an access point 73 of the needleless connector 75.

Figure 9A:
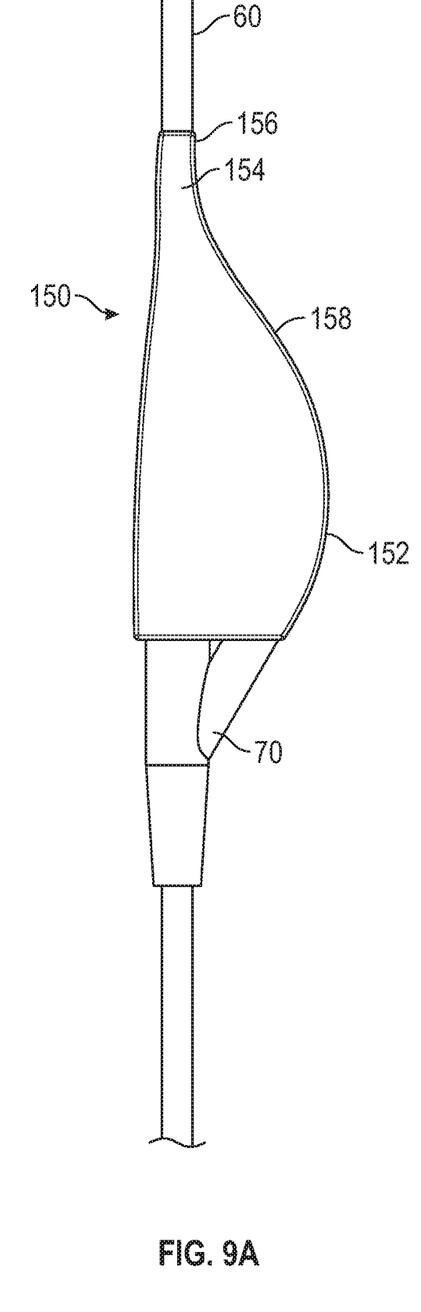
FIGS. 9A-9C depict schematic views of one or more embodiments of an anti-snagging infusion set component in engaged and disengaged positions.
Figure 9B:
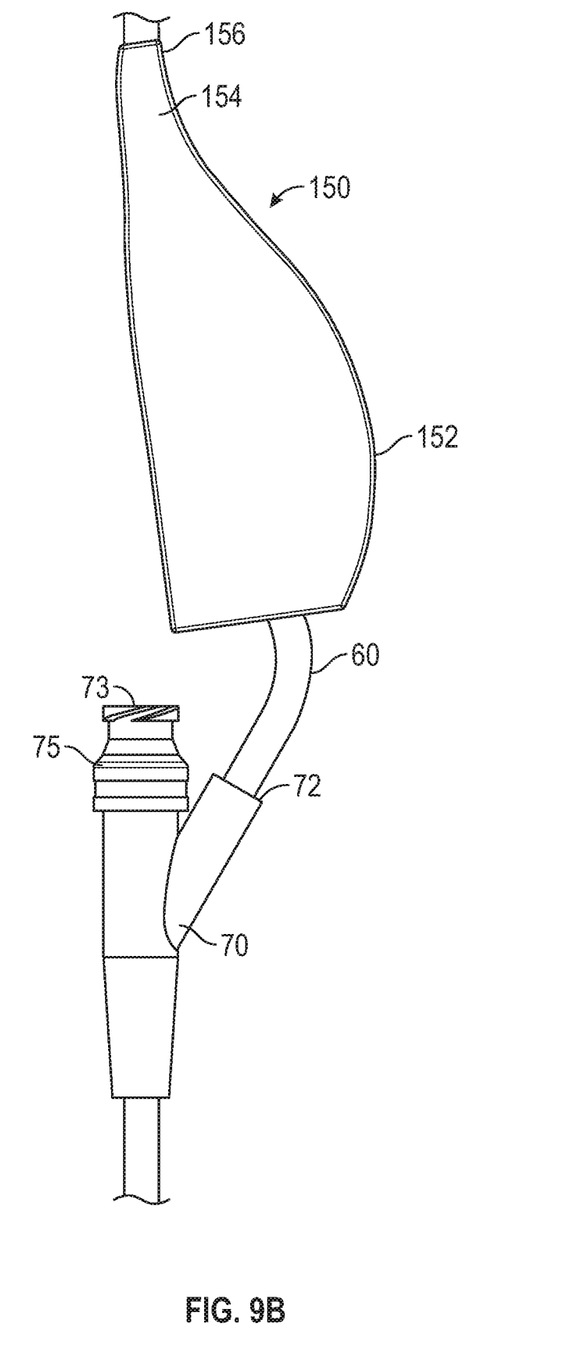
Figure 9C:
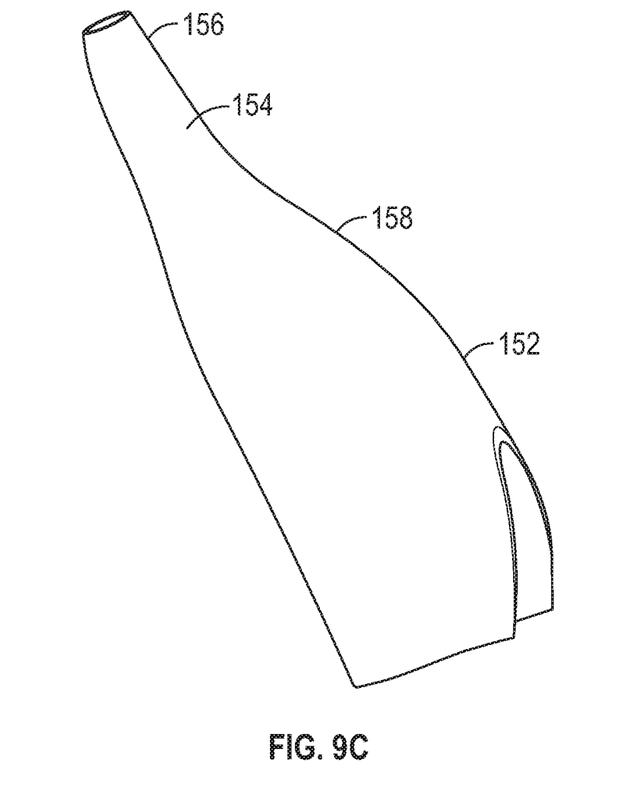

As shown in FIGS. 9A-9C, an anti-snagging structure (e.g., hood) 150 is provided. The hood 150 may have a covering portion 152 and a tail portion 154. The covering portion 152 may be a hood or shroud that is configured to slip over both a needleless connector 75 and an inlet port 72 of a Y-site 70. The covering portion 152 may be a deformable or flexible (e.g., soft) material that stretches as it fits over the top of the Y-site 70. The tail portion 154 may be flexible and have a tube connection point 156 for tethering the tail portion 154 to a tube 60 (e.g., input tube 62). The hood 150 has a sliding surface 158 configured to move the Y-site 70 past a physical object without snagging. The hood 150 may slide onto the tube 60 and then slide towards the Y-site 70 until the covering portion 152 covers some or all of the inlet port 72 and the needleless connector 75. In addition to preventing snagging of the Y-site 70 when the hood 150 is in position, the covering portion 152 has the additional benefit of covering the access point 73 of the needleless connector 75, thus reducing or eliminating contact with contaminants.

Figure 10:
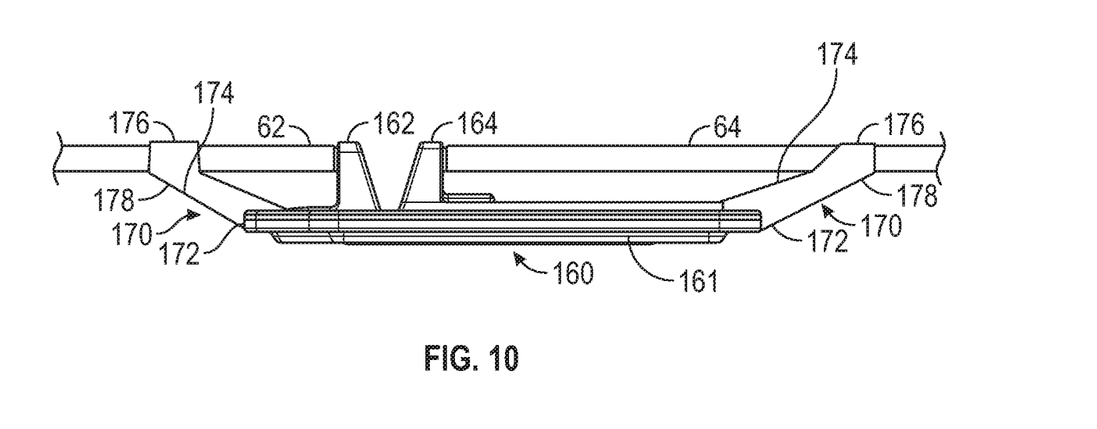
FIG. 10 depicts a schematic view of one or more embodiments of an anti-snagging infusion set filter component.

The infusion set 20 may further include one or more filters 160, as shown in FIG. 10. The filter 160 may have a housing 161, an inlet port 162 that connects to an inlet tube 62 and an outlet port 164 that connects to an outlet tube 64. Fluid may flow through the input tube 62 into the input port 162, through filter elements or materials in the housing 161, and out the outlet port 164 to the outlet tube 64. An anti-snagging structure guide 170 is provided for the filter 160. The guide 170 may have a filter connection portion 172 that may be integrally formed with the housing 161. The filter connection portion 172 may be separately formed and connect to a portion of the housing 161. The guide 170 may also have a tail portion 174 with a tube connection point 176 for tethering the tail portion 174 to the input tube 62 or the output tube 64. The tail portion 174 has a sliding surface 178 configured to move the filter 160 past a physical object without snagging. As shown in FIG. 10, the filter 160 may have a guide 170 disposed at each end of the housing 161, thus minimizing or preventing snagging of the filter 160 when moving in either direction along the longitudinal axis of the filter 160.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

The invention claimed is:

1. An anti-snagging component for use in an infusion set, the anti-snagging component comprising:
   a drip chamber comprising a housing having a fluid input end configured to receive a first intravenous (IV) tube connected to a fluid source and a fluid output end comprising an end surface of the housing; and
   an anti-snagging structure disposed at the fluid output end, the anti-snagging structure comprising:
      a tube port extending from the end surface of the housing, the tube port configured to receive a second IV tube; and
      at least one gusset disposed on the end surface of the housing and the tube port, the at least one gusset extending from a distal most end surface of the housing to a distal most end surface of the tube port, wherein a sliding surface of the at least one gusset extends from the distal most end surface of the housing to the distal most end surface of the tube port and is configured to slidingly guide the housing past an obstruction without snagging when the infusion set is moved, the at least one gusset having a curvilinear triangular shape with a first side disposed on the tube port, a second side disposed on the end surface of the housing and a hypotenuse as the sliding surface, the hypotenuse having a concave surface extending from the end surface of the housing to an end surface of the tube port.

2. The anti-snagging component of claim 1, wherein the at least one gusset is four gussets equally spaced apart about the end surface of the housing.

3. An anti-snagging component for use in an infusion set, the anti-snagging component comprising:
   a drip chamber comprising a housing having a fluid input end configured to receive a first intravenous (IV) tube connected to a fluid source and a fluid output end comprising an end surface of the housing; and
   an anti-snagging structure disposed at the fluid output end, the anti-snagging structure comprising:
      a tube port extending from the end surface of the housing, the tube port configured to receive a second IV tube; and
      at least one gusset disposed on the end surface of the housing and the tube port, the at least one gusset extending from a distal most end surface of the housing to a distal most end surface of the tube port, wherein a sliding surface of the at least one gusset extends from the distal most end surface of the housing to the distal most end surface of the tube port and is configured to slidingly guide the housing past an obstruction without snagging when the infusion set is moved, the at least one gusset having a curvilinear triangular shape with a first side disposed on the tube port, a second side disposed on the end surface of the housing and a hypotenuse as the sliding surface, the hypotenuse having a convex surface extending from the end surface of the housing to an end surface of the tube port.

4. The anti-snagging component of claim 3, wherein the at least one gusset is four gussets equally spaced apart about the end surface of the housing.

5. An anti-snagging component for use in an infusion set, the anti-snagging component comprising:
   a drip chamber comprising a housing having a fluid input end configured to receive a first intravenous (IV) tube connected to a fluid source and a fluid output end comprising an end surface of the housing; and
   an anti-snagging structure disposed at the fluid output end, the anti-snagging structure comprising:
      a tube port extending from the end surface of the housing, the tube port configured to receive a second IV tube; and
      at least one gusset disposed on the end surface of the housing and the tube port, the at least one gusset extending from a distal most end surface of the housing to a distal most end surface of the tube port, wherein a sliding surface of the at least one gusset extends from the distal most end surface of the housing to the distal most end surface of the tube port and is configured to slidingly guide the housing past an obstruction without snagging when the infusion set is moved, the at least one gusset having a triangular shape with a first side disposed on the tube port, a second side disposed on the end surface of the housing and a hypotenuse side as the sliding surface, the hypotenuse side extending from the end surface of the housing to an end surface of the tube port.

6. The anti-snagging component of claim 5, wherein the at least one gusset is four gussets equally spaced apart about the end surface of the housing.

* * * * *